United States Patent [19]
Godolphin et al.

[11] Patent Number: 5,555,920
[45] Date of Patent: * Sep. 17, 1996

[54] METHOD AND APPARATUS FOR ALIQUOTTING BLOOD SERUM OR BLOOD PLASMA

[75] Inventors: William J. Godolphin, Vancouver; Winona C. Specht; David P. Pires, both of North Vancouver; Geoffrey T. Killiam, Burnaby, all of Canada

[73] Assignee: Automed Corporation, Richmond, Canada

[*] Notice: The portion of the term of this patent subsequent to May 18, 2010, has been disclaimed.

[21] Appl. No.: 116,449

[22] Filed: Sep. 3, 1993

Related U.S. Application Data

[63] Continuation-in-part of Ser. No. 57,306, May 5, 1993, Pat. No. 5,413,246, which is a continuation of Ser. No. 693,653, Apr. 30, 1991, Pat. No. 5,211,310.

[51] Int. Cl.$^6$ .................................................... G01N 1/00
[52] U.S. Cl. ............................. 141/329; 141/130; 141/7; 141/59; 141/5; 141/67; 141/285; 141/320
[58] Field of Search ............................... 222/1, 82, 83, 222/83.5, 61, 64, 167, 394, 399, 401, 400.7, 400.8; 422/64, 67, 100, 102; 141/5, 7, 21, 25, 27, 59, 67, 130, 197, 198, 285, 309, 310, 329, 330, 319, 320; 604/411–414

[56] References Cited

U.S. PATENT DOCUMENTS

| | | |
|---|---|---|
| 2,460,641 | 8/1945 | Kleiner . |
| 2,973,758 | 3/1961 | Murrish .............................. 141/330 X |
| 3,288,318 | 11/1966 | Corbin . |
| 3,341,073 | 9/1967 | Arps et al. ........................... 222/400.7 |
| 3,438,549 | 4/1969 | Ritz . |

(List continued on next page.)

FOREIGN PATENT DOCUMENTS

| | | |
|---|---|---|
| 0263753 | 4/1988 | European Pat. Off. . |
| 0285076 | 10/1988 | European Pat. Off. . |
| 0341586 | 11/1989 | European Pat. Off. . |
| 0341587 | 11/1989 | European Pat. Off. . |
| 0348116 | 12/1989 | European Pat. Off. . |

(List continued on next page.)

OTHER PUBLICATIONS

Tecan Robotic Sample Processor Series 5000, 5 pages.
4,169,060, *Official Gazette* notice & abstract, 2 pages, Sep. 25, 1979.
4,847,205, *Official Gazette*, 2 pages, Jul. 11, 1989.
Baxter Healthcare; *New Software MC 2.0* Brochure, 2 pages, Jul. 1990.

(List continued on next page.)

Primary Examiner—J. Casimer Jacyna
Attorney, Agent, or Firm—Klarquist, Sparkman, Campbell, Leigh & Whinston

[57] ABSTRACT

An apparatus and method for dispensing a predetermined volume of liquid from a closed, liquid-containing blood collection tube is described. The apparatus includes a dual conduit providing a passageway for liquid to be dispensed from a closed blood collection tube and a gas conduit providing a passage way for gas to be introduced into the blood collection tube. The apparatus further includes mechanisms for inserting the dual conduit into the blood collection tube, turning the tube away from a vertical and upright orientation, connecting and disconnecting the gas supply to the gas passageway, and providing control over the operation of the mechanisms. A method is also disclosed involving insertion of a dual conduit into a closed blood collection tube, connecting a gas supply to a gas conduit of the dual conduit, rotating the tube away from a vertical, upright orientation, introducing a volume of gas corresponding to a signal into the blood collection tube, receiving a predetermined volume of liquid from the blood collection tube, and physically disconnecting the gas supply from the gas passage way.

9 Claims, 8 Drawing Sheets

U.S. PATENT DOCUMENTS

| | | | |
|---|---|---|---|
| 3,456,647 | 7/1969 | Wada . | |
| 3,484,849 | 12/1969 | Huebner et al. | 141/329 X |
| 3,596,673 | 8/1971 | Laucournet | 137/209 |
| 3,654,925 | 4/1972 | Holderith | 604/413 |
| 3,677,091 | 7/1972 | Guigan . | |
| 3,706,305 | 12/1972 | Berger et al. | 604/413 X |
| 3,782,548 | 1/1974 | Bowen . | |
| 3,849,072 | 11/1974 | Ayres . | |
| 3,885,607 | 5/1975 | Peltier | 141/329 |
| 3,932,277 | 1/1976 | McDermott . | |
| 3,941,171 | 3/1976 | Ogle | 141/309 |
| 4,000,829 | 1/1977 | Johnson, Jr. et al. | 220/265 |
| 4,021,352 | 5/1977 | Sarstedt . | |
| 4,046,699 | 9/1977 | Zine, Jr. . | |
| 4,059,112 | 11/1977 | Tischlinger | 141/329 X |
| 4,131,217 | 12/1978 | Sandegren . | |
| 4,192,438 | 3/1980 | Foster et al. | 222/5 |
| 4,274,453 | 6/1981 | Lee | 141/285 X |
| 4,295,065 | 10/1981 | Hsieh . | |
| 4,296,786 | 10/1981 | Brignola | 141/309 |
| 4,326,959 | 4/1982 | Ferrara . | |
| 4,347,874 | 9/1982 | Sullivan et al. | 141/329 X |
| 4,373,559 | 2/1983 | Mowles et al. | 141/329 X |
| 4,475,914 | 10/1984 | Portnoff | 604/414 |
| 4,478,095 | 10/1984 | Bradley et al. | 73/864.21 |
| 4,522,713 | 6/1985 | Nussbaumer et al. . | |
| 4,532,969 | 8/1985 | Kwaan | 141/27 |
| 4,535,918 | 8/1985 | Heiligman et al. . | |
| 4,583,664 | 4/1986 | Bayat . | |
| 4,630,753 | 12/1986 | Anscherlik . | |
| 4,811,866 | 3/1989 | Golias . | |
| 4,815,325 | 3/1989 | Averette | 73/864.21 |
| 4,861,553 | 8/1989 | Mawhirt et al. . | |
| 4,925,065 | 10/1981 | Hsien . | |
| 4,959,053 | 9/1990 | Jang | 604/127 |
| 4,968,485 | 11/1990 | Morita | 422/100 |
| 4,976,925 | 12/1990 | Porcher et al. . | |
| 4,993,601 | 2/1991 | Nakayama et al. . | |
| 5,019,243 | 5/1991 | McEwen . | |
| 5,030,341 | 7/1991 | McEwen . | |
| 5,033,476 | 7/1991 | Kasai | 604/413 X |
| 5,041,106 | 8/1991 | Noji et al. | 604/411 |
| 5,049,359 | 9/1991 | Azuma | 422/67 |
| 5,065,907 | 11/1991 | Allen . | |
| 5,074,437 | 12/1991 | D'Andrade et al. . | |
| 5,078,970 | 1/1992 | Teodorescu et al. . | |
| 5,151,184 | 9/1992 | Ferkany . | |
| 5,163,582 | 11/1992 | Godolphin et al. | 222/1 |
| 5,211,310 | 5/1993 | Godolphin et al. | 222/1 |
| 5,270,219 | 12/1993 | DeCastro et al. | 141/330 X |

FOREIGN PATENT DOCUMENTS

| | | | |
|---|---|---|---|
| 0409650 | 1/1991 | European Pat. Off. . | |
| 2487680 | 2/1982 | France | 604/412 |
| 2637373 | 4/1990 | France . | |
| 878504 | 10/1961 | United Kingdom . | |
| WO87/05208 | 9/1987 | WIPO . | |
| WOA9219949 | 11/1992 | WIPO . | |
| WOA9310001 | 5/1993 | WIPO . | |

OTHER PUBLICATIONS

Serumax Medical Robotics, 3 pages.

*Idea Caps Risks in Lab,* 1 page, The London Sunday Times, Jan. 24, 1988.

*An Automated Device for Aseptically Aspirating Serum From Blood Collection Tubes,* 7 pages, Jun. 1986; IEEE Translation on Biomedical Engineering.

*Development of a Simple Device for Processing Whole–Blood Samples into Measured Aliguots of Plasma,* 6 pages, 1986; Clinical Chemistry, vol. 32, No. 9.

International Search Report for Application No. PCT/CA92/00181, dated Aug. 5, 1992.

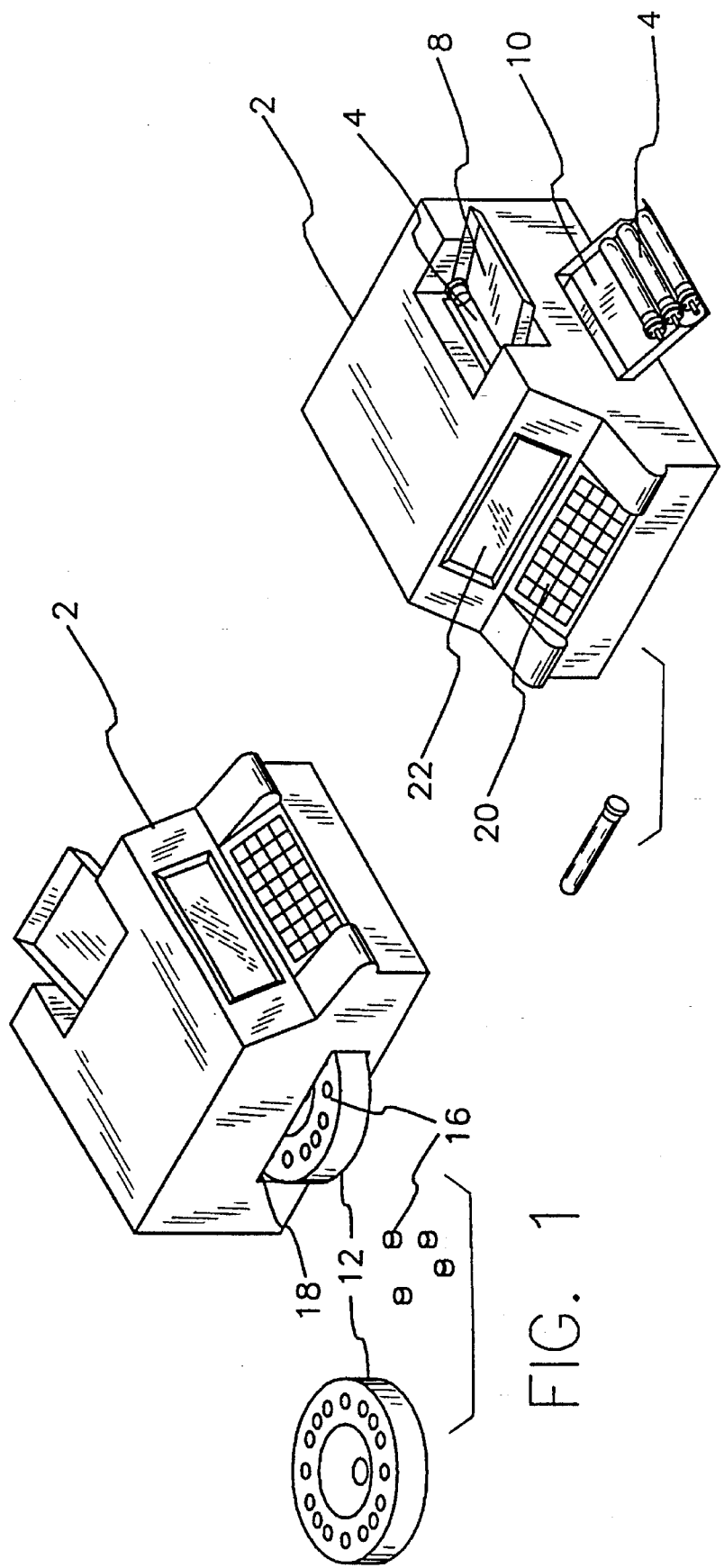

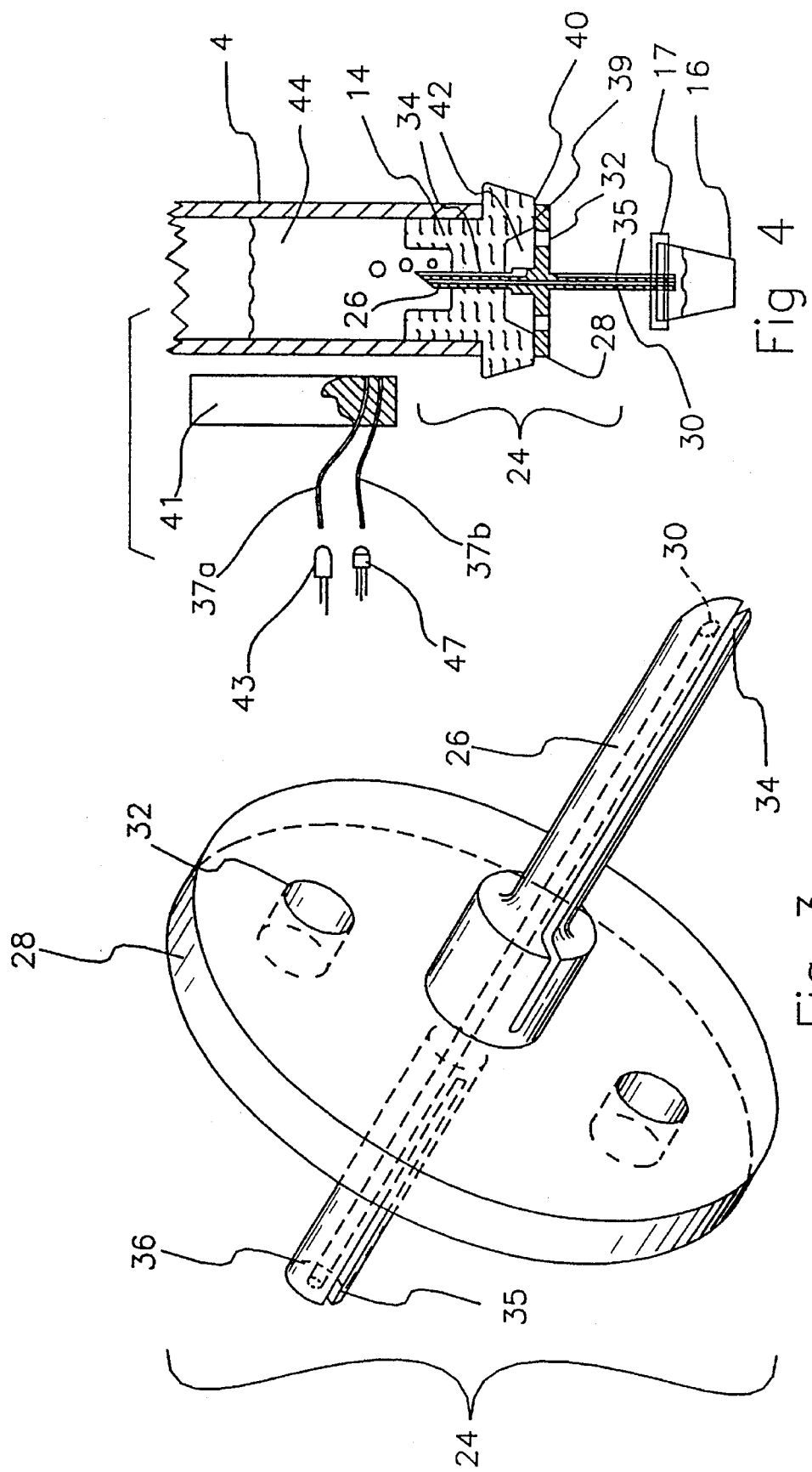

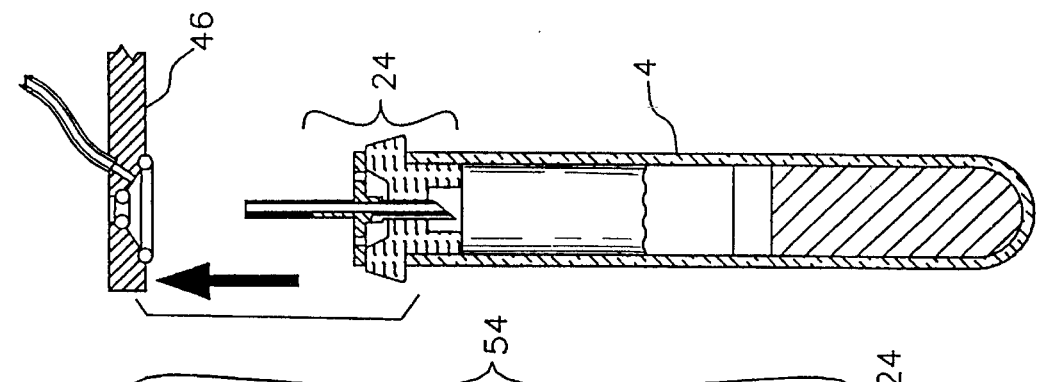
Fig 8
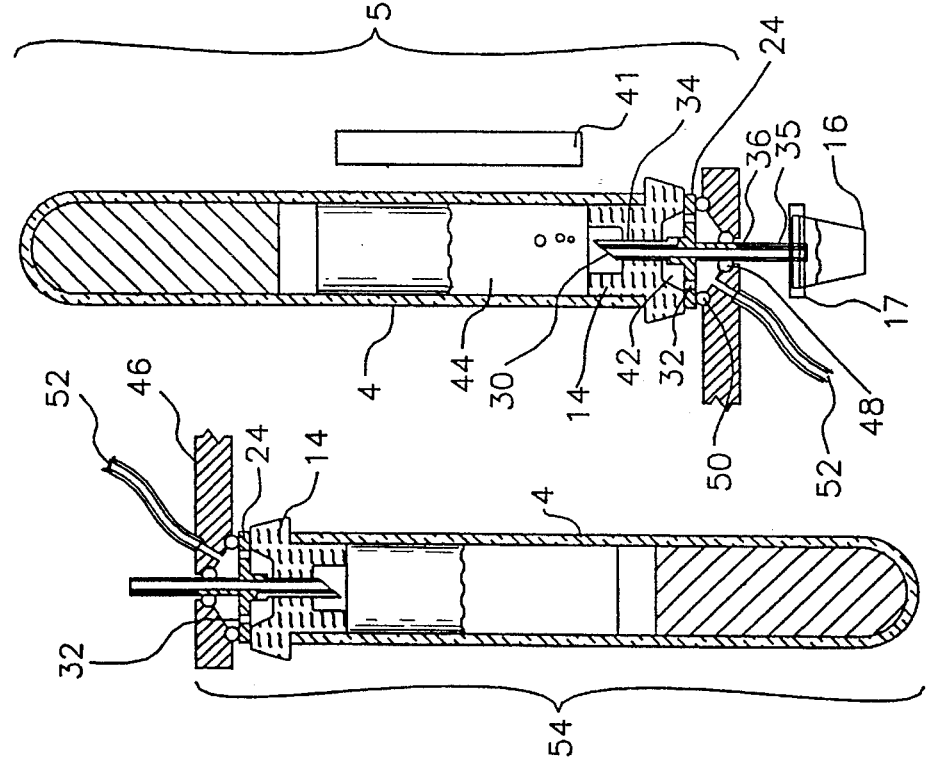
Fig 7
Fig 6
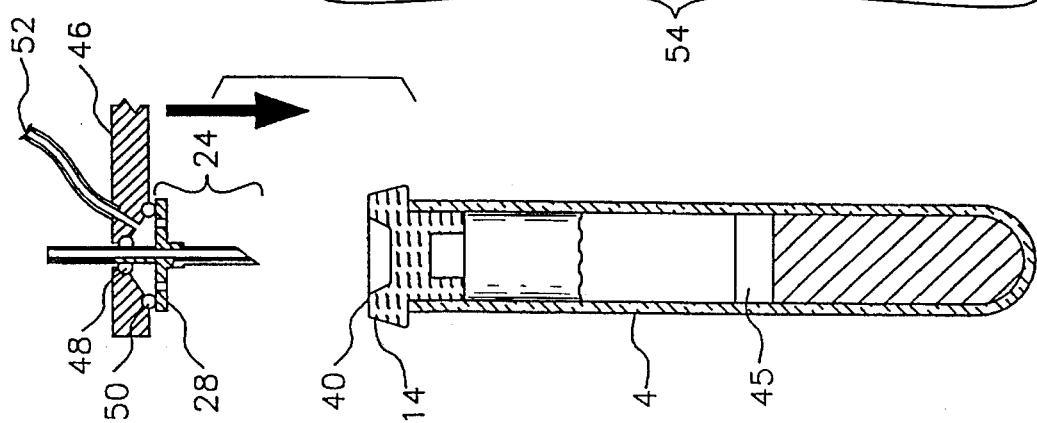
Fig 5

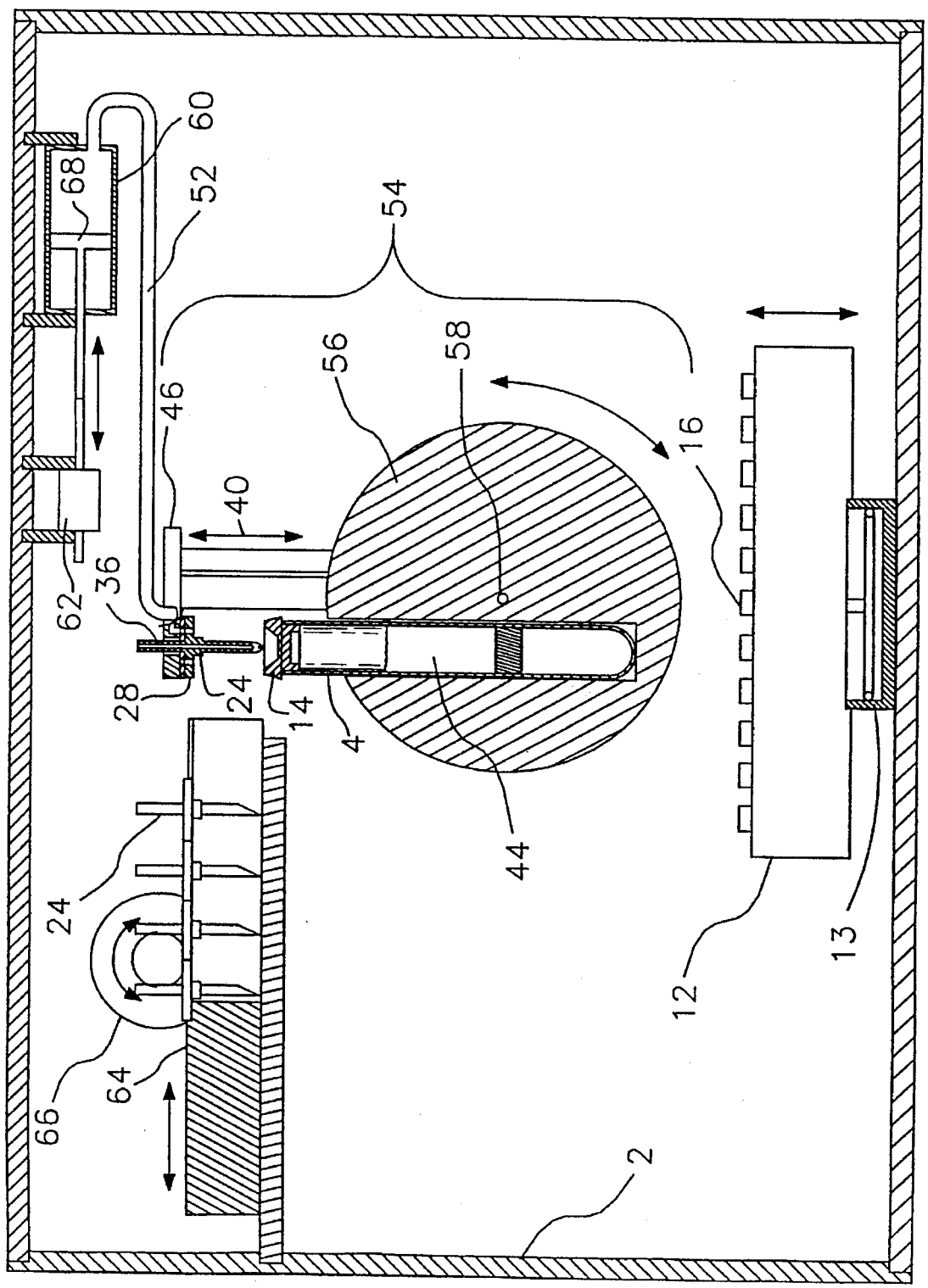

METHOD AND APPARATUS FOR ALIQUOTTING BLOOD SERUM OR BLOOD PLASMA

This application is a continuation-in-part of U.S. patent application Ser. No. 08/057,306 filed May 5, 1993, now U.S. Pat. No. 5,413,246, which is a continuation of application Ser. No. 07/693,653, filed Apr. 30, 1991, now U.S. Pat. No. 5,211,310.

FIELD OF THE INVENTION

The present invention refers to a method and apparatus for dispensing a predetermined volume of liquid from a closed, liquid-containing blood collection tube into a closed receiving vessel. In particular, the invention pertains to dispensing blood plasma or blood sera from a closed blood collection tube for use in clinical analyses.

BACKGROUND OF THE INVENTION

Major sources for concern in clinical laboratories are the safety, costs and efficiency of the normal procedures for preparation of specimens, such as blood, prior to analysis. Blood specimens for clinical analyses are commonly collected in evacuated blood collection tubes. Serum or plasma may be isolated from the cellular material by centrifugation and transferred or aliquotted to one or more specialized sample vessels. These sample vessels are used to introduce a portion of the specimen to chemical analyzers.

The hazards, labour and errors associated with these preanalytic accessioning procedures could be reduced by automation.

Several aspects of the aliquotting procedure must receive critical attention:

(1) The process exposes laboratory personnel to the hazard of direct contact with a biological fluid which may contain infectious agents such as hepatitis or acquired immune deficiency syndrome (AIDS). Technology which reduces or prevents the direct contact by permitting automated removal of serum or plasma from the blood collection tube, without need to remove the stopper would considerably reduce the hazard.

(2) Manual handling of glass apparati (syringes, blood collection tubes, pipettes) exposes technologists to hazards of spillage and breakage and may result in the loss of a specimen of high clinical value. Ideally a sample of serum or plasma should be transferred directly from the collection tube to the recipient vessel without the need to manipulate an intermediary transfer device.

(3) There are many different analyzers in common use. These may have unique sampling vessels. Multiple aliquots must often be prepared from one patient blood specimen into a variety of specialized sample vessels for use in different analyzers. A useful technology would be able to use a wide variety of sample vessels. It would respond to an input signal which identified the analysis required. It would then select and position the appropriate vessel to receive the aliquot(s).

(4) It is often necessary to exclude suspended fibrinous or cellular material, e.g., red blood cells, which may interfere with analyses. A desirable feature of technology for dispensing serum or plasma would be a mechanical filter to remove any suspended particulate material.

(5) The volume transferred may have to be accurately metered, both to conserve the specimen and to provide an optimal amount for a particular analyzer. An automated aliquotter should be able to sense the amount of serum or plasma available and dispense controlled volumes into the various aliquot recipient vessels.

(6) Positive identification of the aliquot, e.g., by label, is necessary since a sample is being transferred from one vessel to another and many other specimens of similar appearance may be handled at the same time. A device for automated accessioning should ensure continuity of identity from the source container (blood collection tube) to each of the aliquots. A preferred means of identity would be a label with a unique identifier which is generated or transferred to the recipient vessel.

(7) Any apparatus which is used to convey sample from a source tube to an aliquot vessel should either be used only once or be thoroughly cleaned between uses. Carry over of less than 1 part per million is desirable and ideally ought to be nil.

(8) Further analyses on any individual or group of specimens may be necessary at a later time, consequently any unused sample is often stored for several days. This must be protected from the effects of evaporation and preserved, usually by refrigeration. The ideal device should prevent evaporation and accidental contamination of the specimen but facilitate removal of further aliquots at a later time.

Conventional sample aliquotting is labor-intensive and has not generally been automated to the same degree as other procedures in clinical laboratories. Automation of sample aliquotting could effectively isolate laboratory personnel from the dangers of blood processing while increasing the speed and efficiency of the overall analytical procedure.

For most analyses of centrifuged blood samples it is necessary to dispense a portion of the sample to alternate containers such as analyzer sample cups. This is done in a number of ways.

In the usual procedure a technologist takes a blood collection tube which has been centrifuged and opens it by removing the stopper from the top. This may create aerosols or splash droplets of infectious serum. Many blood collection tubes are made of glass and the force required to remove the stopper occasionally results in a broken tube. Open or broken tubes increase the risk of sample loss and infectious hazard to the technologist.

A simple disposable transfer pipette is often used to transfer a portion of the serum or plasma. Another popular method of dispensing a sample is to decant an aliquot into the additional recipient containers. If this method is used the blood collection tube must also contain a gel or other barrier such as in U.S. Pat. No. 3,852,194 to Zine to prevent cellular material from being decanted with the serum or plasma. This method is even more hazardous than the first because considerable care and skill is required to decant a small volume of serum or plasma and not to spill any.

Some devices have been made which attempt to address these hazards. One such device is the Tip-Top (TM) Dispenser Cap made by Helena Laboratories of Beaumont Tex. 77704-0752. The Tip Top dispenser is fastened to the open end of a centrifuged blood collection tube, inverted, and then squeezed causing a portion of the sample to be dispensed through an orifice to a sample cup. A disadvantage of the Tip Top dispenser and others like it is that removal of the blood collection tube stopper, a hazardous manual step, is required.

The Pumpette (TM) from Helena Laboratories, Beaumont Tex. 77704-0752 is a disposable, manually operated device which does not require stopper removal to dispense a blood sample from a blood collection tube. However, it delivers only a small stream of serum and its use is slow and cumbersome if large numbers of specimens must be aliquotted quickly.

The CleanTech (TM) system made by CleanTech SCI AG, Langenthal CH-4900, Switzerland consists of several components including a cannula to puncture the stopper, a machine to insert the cannula into the stopper, a pipette to access the sample through the stopper and a pump which fastens to the pipette to draw the sample from the tube. This device goes far to address the hazards of dispensing a sample, but it is a relatively complex device and requires several steps to use.

An important innovation would provide cleaner separation and mechanical filtration of the serum. It is an advantage to detect and avoid aspiration of any fibrous material or to filter it out. Modern analyzers tend to have tiny orifices which are easily clogged by the small clots of fibrin suspended in the serum which may remain or be formed after centrifugation. Some clinical chemistry laboratories filter all serum as a precaution. Filtration may be achieved by a device which is inserted into the open end of the collection tube after centrifugation and permits the one-way flow of serum from the collection tube into a separate sampling container through a filter which prevents fibrin from passing into the serum or plasma sample. Such filtration devices are described, for example, in U.S. Pat. No. 4,464,254 by Dojki and are manufactured and distributed under the name of "serum/plasma filter" by W. Sarstedt, Inc. Other devices have been described by U.S. Pat. No. 3,929,646 by Adler, U.S. Pat. No. 4,602,995 by Cassaday, U.S. Pat. No. 4,487,696 by Ferrara and U.S. Pat. No. 4,142,668 by Lee. However, their use requires additional manipulation of the collection tube, consequent exposure of the user to the blood specimen and risk of contamination of the sample.

A variety of devices have been suggested and used with which sampling is accomplished by means of a cannula inserted through the stopper of a blood collection tube, e.g. Seebaugh WR et al: An automated device for aseptically aspirating serum from blood collection tubes. IEEE Transactions on Biomedical Engineering Vol. BME: 33, No. 6, June 1986, pp 610–616. Such a device may either penetrate the stopper with a large cannula and then insert a smaller one into the serum through the large one (such as on the Paramax (R) Closed Container Sampling (TM) by Baxter, Irvine Calif. 92718; or directly through the stopper as in the Serumax (TM) by Medical Robotics, Inc., Lexington, Ky. 40510. Such systems aspirate part or all of the serum and transfer it to another vessel or directly to the analyzer. A disadvantage of these systems is the need to thoroughly wash all surfaces which contact the serum to reduce analyte carryover from one specimen to another.

Another difficulty with systems which require washing of components which contact the analyte is dilution of the specimen. Systems which require washing generally leave a small residue of water in them after rinsing which then mixes with the next portion of analyte draw into the system. This extra water dilutes the analyte thereby disturbing analytical results.

Some blood collection tubes have been designed to directly incorporate a means to dispense serum, for example U.S. Pat. No. 4,169,060 by Columbus, but these require that all blood specimens be collected in such tubes.

With any cannula which reaches into the serum there is a danger of penetrating or aspirating some of the gel separator material used in some types of blood collection tubes. The Helena Pumpette (TM) has this risk if the operator pushes the fine aspiration tube too far into the tube. The device described by Seebaugh has sensors to detect the gel layer and avoid its penetration by the cannula.

Most systems in the prior art sample from upright tubes and all suffer from the difficulty of monitoring and controlling the depth of sampling. One way to avoid such problems is to sample from closed, inverted tubes. In this way the specimen may be accessed in a way that does not require variable-depth sampling. Some have used this method of sampling, but these systems still have the problems of carryover and dilution.

Aliquots of plasma may be prepared from whole blood with a device such as U.S. Pat. No. 4,847,205 by Burtis. However, the aliquots are very small, being centrifugally distributed into capillaries and the blood must be collected by another apparatus such as a syringe or evacuated blood collection tube and then transferred to this device.

Largely automated aliquotting can be performed with devices such as the Tecan Robotic Sample Processor by Tecan AG, 8634 Hombrechitikon, Switzerland. These devices typically have racks or trays which hold the specimen tube and the vessels for which the aliquots are destined. A sample probe or cannula connected to a pump is manipulated automatically to sip and dispense sample. These devices are generally too inflexible to be of use for the primary aliquotting of samples. They are most suitable for the final dispensing, dilution and sample preparation for a particular analysis, with restricted size and shape of sample and aliquot vessels. Similar robotic systems such as described by U.S. Pat. No. 4,927,545 by Roginski are more flexible in their ability to be adapted to a variety of vessels but require complex programming and use up a great deal of space.

The recipient aliquot containers or sample cups must then be labelled to match the source tube. After one or more aliquots have been dispensed the source tube is usually capped to prevent spillage and evaporation and stored for several days. Occasionally this tube is recovered from storage and more serum or plasma is removed for further testing. The additional cap is an added expense, whereas if the original stopper is used there is increased contact with the hazardous biological fluid.

SUMMARY OF THE INVENTION

The present invention relates to an apparatus and method for dispensing a liquid such as blood, blood sera, or blood plasma from a closed, liquid-containing blood collection tube into a closed receiving vessel.

The invention includes an apparatus having a dual conduit providing a gas passage way for gas to be introduced into a blood collection tube and providing a liquid passage way for liquid to be dispensed out from the blood collection tube. The apparatus also includes a means for inserting the dual conduit into the blood collection tube and a means for rotating the blood collection tube away from a vertical, upright orientation. Also included is a means for connecting a gas supply to the gas passage way of the dual conduit and a means for displacing, in response to a signal, a volume of gas into the tube through the gas passage way to displace a predetermined volume of liquid from the tube. A means of controlling the operations of the apparatus is also described. The apparatus further provides means for inserting the dual conduit means through the cap of a receiving vessel so that liquid may be dispensed out of the blood collection tube and into the receiving vessel without removing the cap of the receiving vessel.

Also disclosed is a method including the steps of inserting a dual conduit means into a blood collection tube in response to a generated signal, connecting a gas supply to the gas passage way of the dual conduit means, rotating the blood collection tube away from a vertical, upright orientation, introducing a volume of gas into the blood collection tube through the gas passage way, receiving from the blood collection tube through the liquid passage way of the dual conduit a predetermined volume of liquid, and disconnecting the gas supply from the gas passage way. Also included is a method of controlling the process.

Also described is a liquid sensing means for generating a signal representative of the amount of liquid contained within a blood collection tube, a data input means for indicating the amount of liquid to be dispensed from a blood collection tube, and a control means to regulate the introduction of a gas into a blood collection tube according to a comparison of signals provided by the data input means and the liquid sensing means.

BRIEF DESCRIPTION OF THE DRAWINGS

FIG. 1 shows the automated aliquotter module indicating the position of the analyzer tray containing analyzer cups.

FIG. 2 shows another view of the automated aliquotter module illustrating the input and output trays for blood collection tubes.

FIG. 3 shows the disposable pipetter which is used within the automated aliquotter module, or a manually operated embodiment of the aliquotter, to facilitate dispensing of serum/plasma from a closed blood collection tube.

FIG. 4 shows a disposable pipetter used with a centrifuged blood collection tube.

FIG. 5 shows an automated aliquotter module inserting a disposable pipetter into the stopper of a closed blood tube.

FIG. 6 shows a disposable pipetter having been inserted through the stopper of a closed blood tube.

FIG. 7 shows the automated aliquotter module having inverted a tube is dispensing fluid through a disposable pipetter into an analyzer cup.

FIG. 8 shows a blood tube which has had a portion of its contents dispensed being ejected from the automated aliquotting module.

FIG. 9 shows the mechanisms used to manipulate a sample tube within the aliquotter module and to facilitate dispensing of fluid from a sample tube illustrating the operation of the automated aliquotter.

DESCRIPTION OF SPECIFIC EMBODIMENTS

Figures 10, 11, 12, 13:
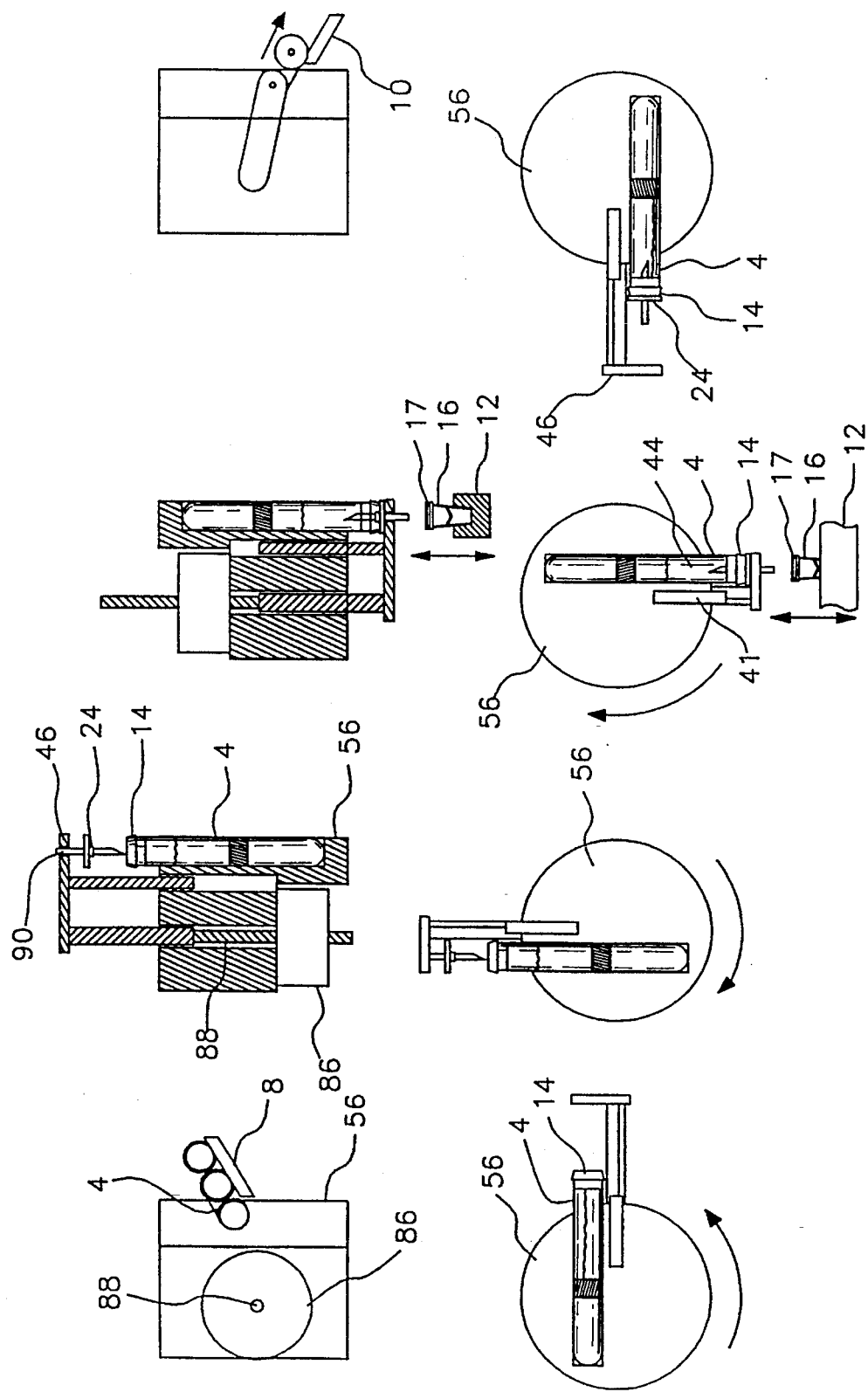
FIG. 10 shows tubes in an input region and how the automated aliquotter module receives a single tube to be aliquotted.
FIG. 11 shows the automated aliquotter positioning a blood tube in an upright position to receive a disposable pipetter.
FIG. 12 shows the aliquotter inverting a blood tube in order to dispense a portion of the liquid contained within it into an analyzer cup.
FIG. 13 shows the aliquotter ejecting a tube that has been aliquotted.

The present invention is an apparatus for dispensing a specimen of liquid from a closed container and directing the liquid into one or more subcontainers. More specifically, the present invention is an apparatus for dispensing blood, blood sera or blood plasma from a blood collection tube into analyzer sample cups to be used within automated blood analyzers. In the following description the disposable component of the invention is termed "disposable pipetter" and the machine component is termed "aliquotter module".

FIG. 1 shows one view of the preferred embodiment of the present invention showing the general form of the machine component as it would appear in use. An analyzer tray 12 is shown positioned in output bay 18 of the aliquotter module 2. The analyzer tray holds a multiplicity of small analyzer cups 16 which receive a portion of liquid from a blood collection tube being processed within aliquotter module 2. When a number of analyzer cups have received a liquid portion, the analyzer tray 12 is manually removed from the aliquotter module 2 and placed into an automated analyzer, such as are common in many clinical laboratories, where the dispensed portions are analyzed. FIG. 2 shows another view of the aliquotter module 2 better showing the input tray 8 and output tray 10. Input tray 8 receives one or more blood tubes 4 which are individually received and processed by aliquotter module 2. Output tray 10 receives blood tubes 4 one by one from aliquotter module 2 after a portion of each one's contents have been dispensed. The tubes in output tray 10 are periodically removed by hand to be stored for later reference or are disposed of.

Again referring to FIGS. 1 and 2, aliquotter module 2 receives a liquid-containing blood tube in input tray 8, accepts the blood tube from the input tray, identifies the blood tube using a barcode reader, measures the quantity of liquid within the blood tube, dispenses the liquid contained within the tube into one or more analyzer cups 16 which are located in analyzer tray 12, and then ejects the processed blood tube into output tray 10. The amount of liquid to be dispensed in each dispensing operation is predetermined on the basis of information about the sample such as analyte volume, sample quality, test requisitions and test priority. Aliquotter module 2, having dispensed from a blood tube a predetermined amount of liquid into one or more analyzer cups 16, then ejects the blood tube from the aliquotter into output tray 10. Analyzer tray 12 may then be removed from the apparatus by the operator to be taken to the appropriate analyzer for analysis of the liquid contained in the analyzer cups.

Still referring to FIG. 2, the preferred embodiment of aliquotter module 2 has a keyboard 20 for data input and a display screen 22 to relay important information to an operator. The keyboard 20 allows a user to control the parameters of the machine and to input information regarding a blood sample that is being aliquotted by the apparatus. The display screen 22 provides a confirmation of what has been typed on the keyboard as well as supplying error messages and information about said blood sample. The keyboard and display portions of the apparatus are of a type found on many electronic devices.

Figure 14:
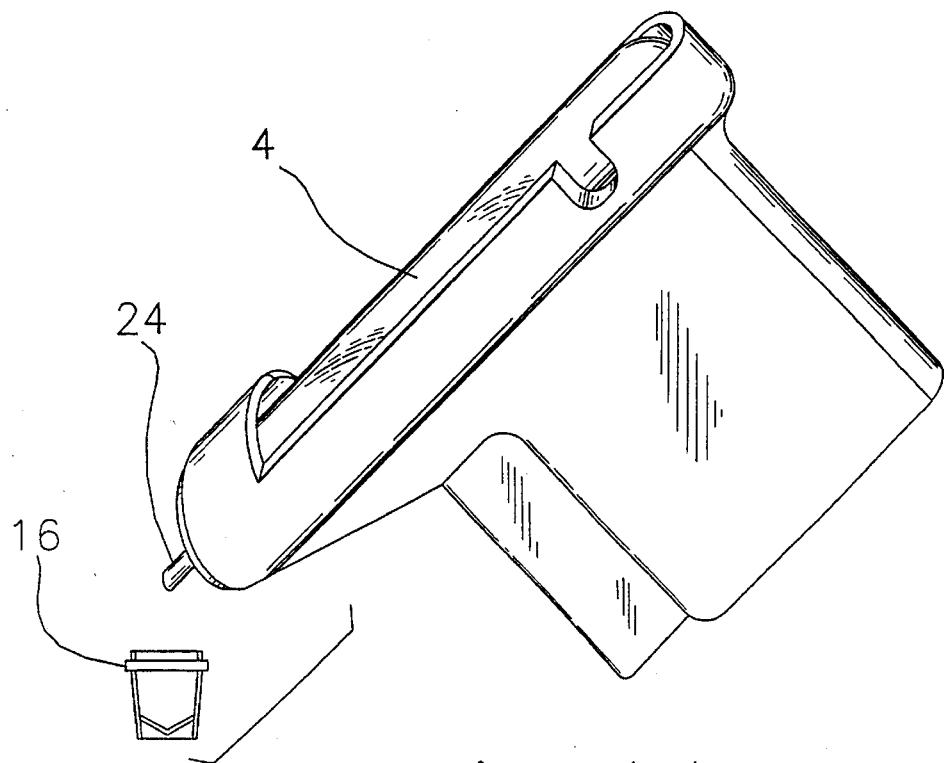
FIG. 14 shows a hand-operated implementation of the aliquotter module for use in a non-automated environment.

FIG. 3 shows disposable pipetter 24 which is used within the aliquotter module 2 of FIGS. 1 and 2 or within a manually operated aliquotting device (depicted in FIG. 14)

to dispense a portion of liquid from a closed, liquid-containing blood collection tube. Disposable pipetter 24 is preferably injection molded in one piece of polystyrene or other substantially hard plastic. Disposable pipetter 24 is fashioned so as allow liquid to be expressed from a blood tube 4 by providing for a gas such as air to be forced into the tube (pressurizing the interior of the tube) causing liquid to be expressed from the tube through serum conduit 30. The disposable pipetter comprises a stopper spike 26, base plate 28, serum conduit 30, air inputs 32, air groove 34, and serum spout 36. Air groove 34 is made small enough to allow the passage of pressurized gas into the tube, but to resist the flow of fluid out of the blood tube. Air groove 35 located on serum spout 36 permits the escape of air from a closed receiving vessel when serum spout 36 is inserted through a tight fitting cap on the receiving vessel.

FIG. 4 shows the disposable pipetter 24 as it appears in use. The stopper spike 26 punctures tube stopper 14 and the pipetter 24 is pushed onto the tube stopper until the base plate 28 is comes to rest against the stopper rim 40. The disposable pipetter 24 is held against the stopper (by a mechanism depicted in FIGS. 5 through 9) causing plate 28 to seat against the stopper rim 40 thereby making air-tight seal 39 where stopper rim 40 engages base plate 28. Once disposable pipetter 24 has been thus positioned, the tube is inverted so that liquid 44 contained in blood tube 4 rests in the stopper end of the tube above the stopper spike 26 of the disposable pipetter 24 as shown. Once inverted, analyzer cup 16 is moved upward to cause serum spout 36 to penetrate cap 17. With the blood tube in the inverted position, the volume of the liquid contained therein may be measured optically. If the tube were not inverted it would be more difficult to measure the volume of blood serum or plasma contained therein because the unknown volume of cellular matter in the bottom of the tube affects the surface level of the liquid portion. With the tube inverted the volume of liquid is always measured from the datum of the stopper. The volume of liquid is then measured by liquid level sensor 41. A metered amount of air is then forced through the air inputs 32, into the airgap 42, and further through air groove 34 pressurizing the interior of the blood tube 4. As the blood tube 4 is pressurized, liquid 44 is forced through the serum conduit 30 thereby dispensing it from tube 4 into closed analyzer cup 16. Cap 17 of sample cup 16 is made of a material which is easily punctured by serum spout 36 (which can be shaped with a taper or point for piercing the cap), or has small slits cut into it so that serum spout 36 can open the slits and penetrate the cap as sample cup 16 is raised. Stopper spike 26 is made just long enough so that serum conduit 30 reaches just inside of the blood tube with an opening positioned proximal to the interior surface of the tube stopper 14 so that when liquid is being dispensed, virtually all the liquid within the tube is accessible. If the stopper spike 26 was too long there would be a certain volume of liquid which could not be accessed by the method of this invention because there would be some liquid positioned between the opening of the liquid path and the interior surface of the stopper. Therefore the length of the stopper spike 26 is made just long enough to reach just inside the thickest stoppers that are to be processed. When processing tubes with thinner stoppers there would be a small amount of inaccessible liquid. The tip of stopper spike 26 may be made of a porous material and made of so that it covers serum conduit 30 thereby providing a filter function in the tip of stopper spike 26. The filter function can also be achieved by making the opening of serum conduit 30 very small. This is an effective way to keep fibrin and other particulate from being dispensed into sample cup 16.

Again referring to FIG. 4, liquid level sensor 41 consists of a group of light emitting diodes 43 interleaved with optical sensors 47 which utilize optical fibers 37a and 37b to position the sensors and light sources in a fine linear array within level sensor 41. The light from light emitting diode 43 shines through optical fiber 37a into the interior of tube 4 illuminating the contents of the tube. Optical sensor 47 receives reflected light through optical fiber 37b indicative of the contents of the tube nearest to that fiber. An optical fiber that is located near a portion of the tube that has air just on the other side of the tube wall receives a different amount of light than an optical fiber that is positioned at a portion of the tube that has liquid just on the other side of the tube wall. In this way, knowing the position of the optical fibers which show an air/liquid interface and knowing the position of the interior surface of stopper 14 it is possible to calculate the volume of liquid 44 contained within tube 4. The volume of available liquid is an important piece of information for aliquotting blood serum or plasma for analysis because if there is not enough serum or plasma to accomplish all of the desired tests, the automated aliquotter (or an operator) must make decisions about how to best dispense the liquid to accomplish the most important tests. Chromatic filters may be used within level sensor 41 in order to determine various sample quality parameters. For instance, hemolysis (characterized by red serum), icteris (characterized by very yellow serum) and lipemia (characterized by turbid serum) may be sensed by level sensor 41 equipped with appropriate chromatic filters and be measured using colormetric methods known in the art.

FIGS. 5 to 8 illustrate the steps required to aliquot a sample according to the method of the present invention.

FIG. 5 shows the first step of inserting a disposable pipetter 24 into the stopper of a separated blood tube 4. Blood tube 4, as depicted here, is of the type commonly used for blood collection and separation in the clinical laboratory and is of the type that has a physical barrier 45 like that found in the SST Vacutainer TM made by Becton-Dickinson of Franklin Lakes, N.J. Disposable pipetter 24 is shown held in pipetter holder 46. Pipetter holder 46 includes inner seal 48, outer seal 50, and air supply 52. Pipetter holder 46 and blood tube 4 are brought together under sufficient force to cause disposable pipetter 24 to puncture through tube stopper 14 and for base plate 28 to come to rest against stopper rim 40.

FIG. 6 shows the disposable pipetter 24 in its rest position after insertion into the tube stopper 14.

After the disposable pipetter 24 is inserted into the stopper 14 the integrated assembly 54 comprising the blood tube 4, pipetter holder 46, and the disposable pipetter 24 is inverted as shown in FIG. 7. Once the integrated assembly 54 has been inverted, the liquid 44 comes to rest above stopper 14 and disposable pipetter 24 in the position shown. The volume of liquid available is then measured by liquid level sensor 41. Analyzer cup 16 is then raised to cause serum spout 36 to penetrate cap 17 in preparation to receive liquid such as serum or plasma from serum spout 36. A controlled amount of air is then forced through air supply 52, though air inputs 32 into airgap 42 and further through air groove 34 thus pressurizing the interior of blood tube 4. Pressurizing the interior of blood tube 4 forces some of liquid 44 to pass through serum conduit 30 dispensing it from serum spout 36 into analyzer cup 16. As analyzer cup 16 fills, any air displaced by the volume of liquid forced into analyzer cup 16 escapes past cap 17 via air groove 35. When the correct amount of serum or plasma is dispensed, analyzer cup 16 is lowered so that serum spout 36 is withdrawn from cap 17.

More than one analyzer cup 16 may be used for a single blood tube by dispensing liquid 44 in successive dispensing operations. Inner seal 48 and outer seal 50 seal against disposable pipetter 24 so as to confine gas to pass from air supply 52 through air inputs 32.

After a specific amount of serum or plasma has been dispensed from the tube into one or more sample cups pipetter holder 46 moves away from blood tube 4 and the blood tube together with the disposable pipetter 24 is released from pipetter holder 46 and is either stored for later testing or is disposed of. FIG. 8 illustrates this release action. Although this phase of the operation is shown with the tube in a vertical orientation, it is not necessary that it be so.

FIG. 9 illustrates the automated aliquotter module in a simplified form showing important mechanical elements of the apparatus. Blood tube 4 is shown in tube cradle 56 which rotates about axle 58 in preparation for dispensing fluid according to the method depicted in FIGS. 5 to 8. Pipetter holder 46 is located on tube cradle 56 and moves as shown under the influence of an electric motor in order to push pipetter 24 through stopper 14 and to hold pipetter 24 and tube 4 in place when cradle 56 is rotated. The movement of pipetter holder 46 and other machine motions may be achieved by other means such as pneumatic, hydraulic, or even manual means and therefore the use of an electric motor does not constitute a limitation of the present invention. Also shown is gas cylinder 60 which is actuated by linear drive motor 62 to supply a metered amount of gas to be injected into tube 4 causing fluid to be dispensed according to the method of the invention. Pipetter carriage 64 supplies disposable pipetters 24 to pipetter holder 46 in an automated fashion so that the apparatus may process a number of blood tubes one at a time each one using a pipetter. Carriage motor 66 moves disposable pipetters 24 into a position accessible to pipetter holder 46. Also shown is analyzer tray 12 holding a number of analyzer cups 16. Analyzer tray is rotated about a central axis in order to position an analyzer cup 16 beneath serum spout 36 of a tube that has been inverted by cradle 56 and that is to have its contents dispensed.

In use, the apparatus depicted in FIG. 9 functions in the following way. Pipetters 24 are loaded into pipetter carriage 64 by an automated handler (not shown) or by hand in preparation for the operation of aliquotter module 2. Blood tube 4, which is to have its contents dispensed into analyzer cups 16, is loaded into tube cradle 56 in an automated fashion depicted in FIG. 10 or by hand. Pipetter holder 46 receives a disposable pipetter 24 from pipetter carriage 64. When blood tube 4 has been positioned in tube cradle 56 and pipetter holder 46 has positioned disposable pipetter 24 as shown, pipetter holder 46 moves disposable pipetter 24 so that it punctures stopper 14 of blood tube 4 and continues to supply a force to hold the tube within cradle 56 and to cause base plate 28 to seal against stopper rim 40. Integrated assembly 54 is then inverted so that serum spout 36 is positioned above an analyzer cup 16. With the assembly inverted, it is possible to optically determine the volume of dispensable liquid within the blood tube for purposes of making decisions regarding how the sample should be divided between subcontainers. Once serum spout 36 is directly above analyzer cup 16, elevator 13 raises analyzer tray 12 so that serum spout 36 penetrates the cap of analyzer cup 16. When this is done, linear drive motor 62 under automated control or manual control, moves piston 68 so that air is forced through air supply 52, through the disposable pipetter, and into the inverted blood tube. As air is forced into blood tube 4 the liquid contained therein is displaced through serum conduit 30 and into an analyzer cup 16. If additional analyzer cups need to be filled, linear drive motor 62 stops (thereby preventing further liquid to be dispensed from the blood tube), elevator 13 lowers analyzer tray 12 and analyzer tray 12 is rotated so that a different analyzer cup is positioned beneath serum spout 36. When a new analyzer cup is positioned beneath the serum spout, elevator 13 raises analyzer tray 12 to cause serum spout 36 to penetrate the cap of the new analyzer cup, and linear drive motor 62 is again engaged causing more of liquid 44 to be dispensed according to the procedure outlined above. This procedure may be repeated to fill several sample cups. When a sufficient amount of liquid 44 is dispensed from blood tube 4 then blood tube 4 and disposable pipetter 24 are removed together from the apparatus by manual or automated handling means. The resulting blood tube/pipetter assembly is then stored for later use or is disposed of.

FIGS. 10 to 13 illustrate further the operation of the automated aliquotter module. Each of the figures show a front view beneath a side view of tube cradle 56, blood tube 4, and pipetter holder 46.

Referring to FIG. 10, blood tube 4 is loaded into tube cradle 56 by gravity from input tray 8. In this way a single blood tube is loaded in preparation for dispensing the contents of the tube. Tube cradle 56 then rotates until it is in the position indicated by FIG. 11. In FIG. 11 pipetter holder 46 is shown as it is about to insert disposable pipetter 24 into stopper 14 of tube 4. Once pipetter 24 has been positioned by pipetter carriage 64 of FIG. 9 as shown, clamping motor 86 turns lead screw 88 causing pipetter holder 46 to move towards blood tube 4. Pipetter holder 46 is stopped momentarily when it has grasped disposable pipetter 24 so as to allow pipetter carriage 64 (FIG. 9) to move out of the way. Pipetter holder 46 grabs hold of pipetter 24 by means of a tight-fitting hole 90. Pipetter holder 46 then continues to move toward blood tube 4 until pipetter 24 is pierced through tube stopper 14 and is clamped against said stopper. Once disposable pipetter 24 is fully inserted into stopper 14 and is clamped, tube cradle 56 rotates so as to position blood tube 4 and disposable pipetter 24 as shown in FIG. 12. When the position shown in FIG. 12 is achieved, the volume of available liquid can be measured by liquid level sensor 41. A controlling computer (or the operator) then uses the volume information together with information regarding sample cup type, test requisitions, sample quality, and test priority to determine the most optimal division of the liquid among a number of sample cups. Liquid 44 is then dispensed in amounts corresponding to signals provided by the operator or the controlling computer. Once a desired amount of liquid has been dispensed into one or more subcontainers, tube cradle 56 is rotated further into the position illustrated by FIG. 13. FIG. 13 shows how a blood tube that has been aliquotted is unloaded from the aliquotter. Once tube cradle 56 has been rotated to the position shown, pipetter holder 46 is moved away from blood tube 4 leaving disposable pipetter 24 in tube stopper 14. Blood tube 4 with disposable pipetter 24 then moves into output tray 10 under the influence of gravity. Tubes that are found in output tray 10 are later removed manually for storage or disposal.

An alternate embodiment of the present invention is shown in FIG. 14. Although this implementation is a manually operated one, it still functions following the method of the present invention. Disposable pipetter 24 is inserted onto blood tube 4, the tube is then inverted and a gas such as air is injected into tube 4 causing liquid 44 to be dispensed from disposable pipetter 24 into analyzer cup 16. Insertion of disposable pipetter 24 into the stopper of blood tube 4 may be accomplished manually. If this alternate embodiment is used to re-aliquot a sample which was previously had a portion of its contents dispensed by an automated aliquotter (shown in FIG. 1), a disposable pipetter will have already been inserted into the stopper of blood tube 4 and it may be used again.

Figure 15:
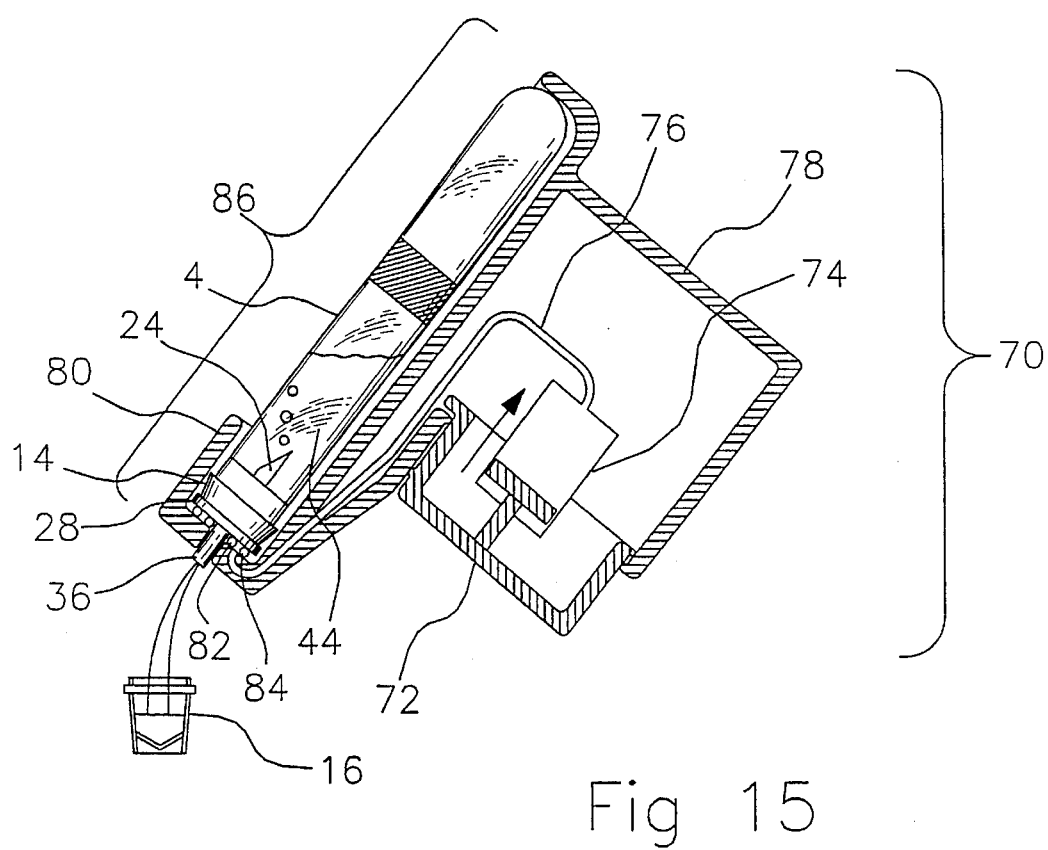
FIG. 15 shows a cross-sectional view of the hand-operated aliquotter indicating how its functions are accomplished.

FIG. 15 shows a cross-sectional view of the alternative embodiment of the aliquotter module. Components of the manual aliquotter module 70 include trigger 72, air pump 74, air line 76, handle 78, tube holder 80, inside seal 82 and outside seal 84. Also shown are the blood tube 4, disposable pipetter 24 and analyzer cup 16.

In use, disposable pipetter 24 may be manually inserted through stopper 14 of blood tube 4 in preparation for dispensing a portion of the liquid contained in blood tube 4 into an analyzer cup 16. Assembly 86 resulting from the union of blood tube 4 and pipetter 24 is then loaded into manual aliquotter module 70 by inserting the pipetter end of assembly 86 in the end of tube holder 80 which contains inside seal 82 and then forcing assembly 86 into the position illustrated in the figure. As assembly 86 is being thus positioned within manual aliquotter module 70, inside seal 82 and outside seal 84 press against base plate 28 of disposable pipetter 24 to create a confined path for air to be forced from air pump 74 through pipetter 24 into tube 4 thereby causing liquid 44 to be dispensed from assembly 86 into analyzer cup 16. Once assembly 86 has been positioned and said seals have been established then manual aliquotter module 70 is positioned so that liquid 44 is positioned substantially above stopper 14 as shown. Trigger 72 is then depressed in the direction indicated by the arrow causing air pump 74 to displace air through air line 76, between inside seal 82 and outside seal 84, and further through disposable pipetter 24 into blood tube 4. As this air is displaced into tube 4, liquid 44 is then forced out of serum spout 36 into analyzer cup 16. In this way liquid can be easily and safely dispensed from a closed blood collection tube using the apparatus and method of the present invention.

Figure 16:
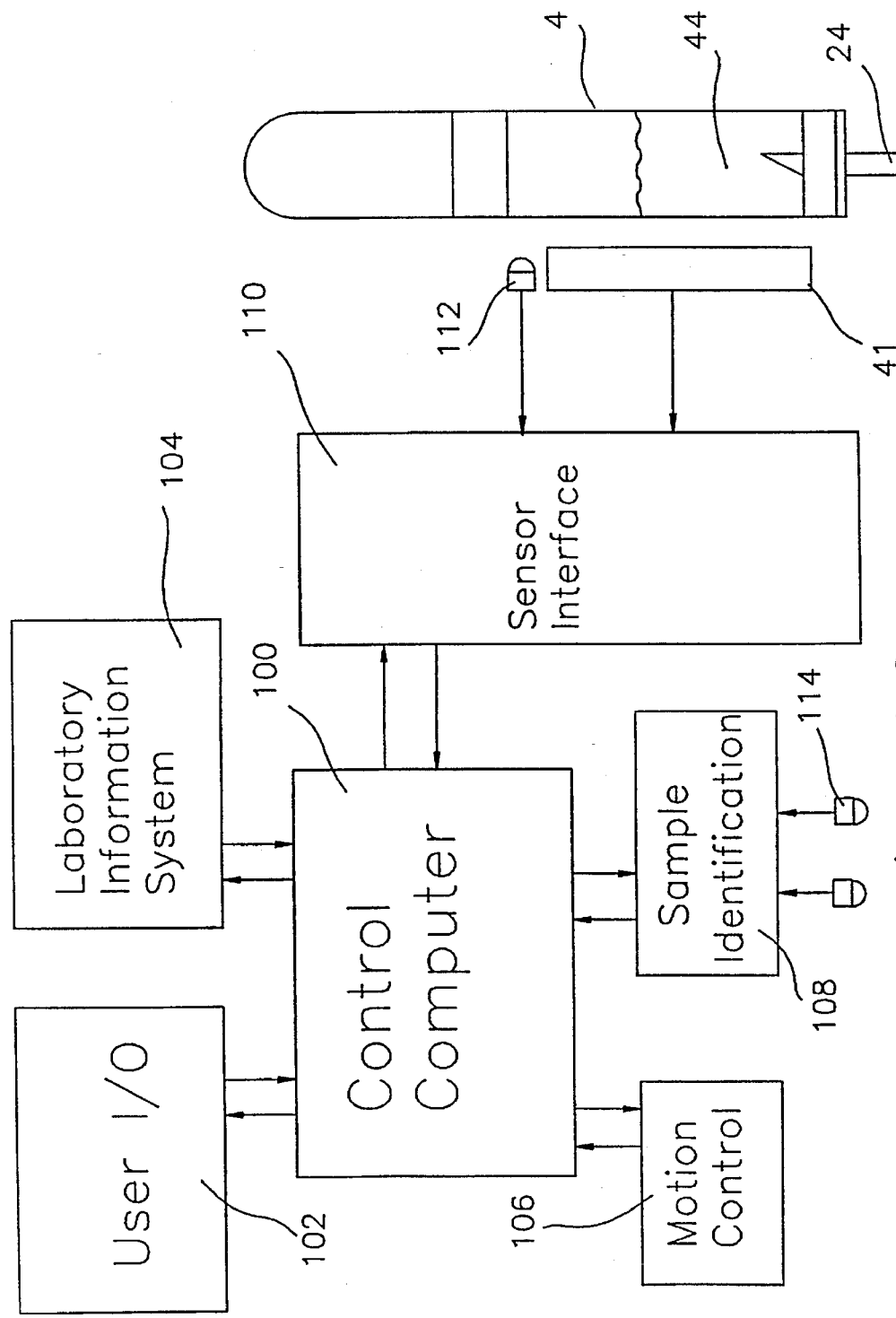
FIG. 16 shows the process control system for the automated aliquotter.

FIG. 16 shows the process control system for the automated aliquotter in block diagram form. Control computer 100 controls the automated aliquotter utilizing user supplied information, sensor-derived information, and laboratory database information. User supplied information enters via user I/O port 102 which, in the preferred embodiment, includes an alphanumeric keypad. Control computer 100 also relays process and control information to the user through the user I/O port 102. Information regarding sample identification and patient information contained within the laboratory database is relayed to and from control computer 100 through laboratory information system 104. Laboratory information system 104 is of a type typical in many large laboratories. Motion control module 106 drives the various mechanical motions of the aliquotter by powering motors according to signals provided by control computer 100. Said motors include linear drive motor 62 of FIG. 9 receiving said signals for dispensing a predetermined volume of sample liquid 44. Position and other information about the status of the motion systems is fed back to control computer 100 through motion control module 106. Sample identification module 108 allows barcode readers 114 to be interfaced with control computer 100 for the purpose of identifying blood tubes and sample cups. This is an important aspect of the control system because sample identification links the blood sample to information required to determine which test requisitions are to be performed on the present sample and how the sample is to be divided. Sensor interface 110 receives signals from various sensors and converts these signals into a form which can be used by control computer 100. These sensors include serum quality sensor 112 and liquid level sensor 114 as well as various process and status sensors. Serum quality sensor 112 and liquid level sensor 41 provide information to control computer 100 for making decisions about how to divide a sample among several sample cups for performing various tests. There may be more than one serum quality sensor 112 and each one may be configured to provide an indication of a different sample parameter.

Since many changes can be made in the construction of the above disposable pipetter, aliquotter module, and sensing apparatus, and applications of the machine and process of the present invention without departing from the scope thereof, it is intended that all matter contained in the above description or shown in the accompanying drawings shall be interpreted as illustrative and not in the limiting sense. Examples would be modification of the general shape of the disposable pipetter, variations in the control system, or a different configuration of the tube cradle and clamping mechanism.

Figure 17:
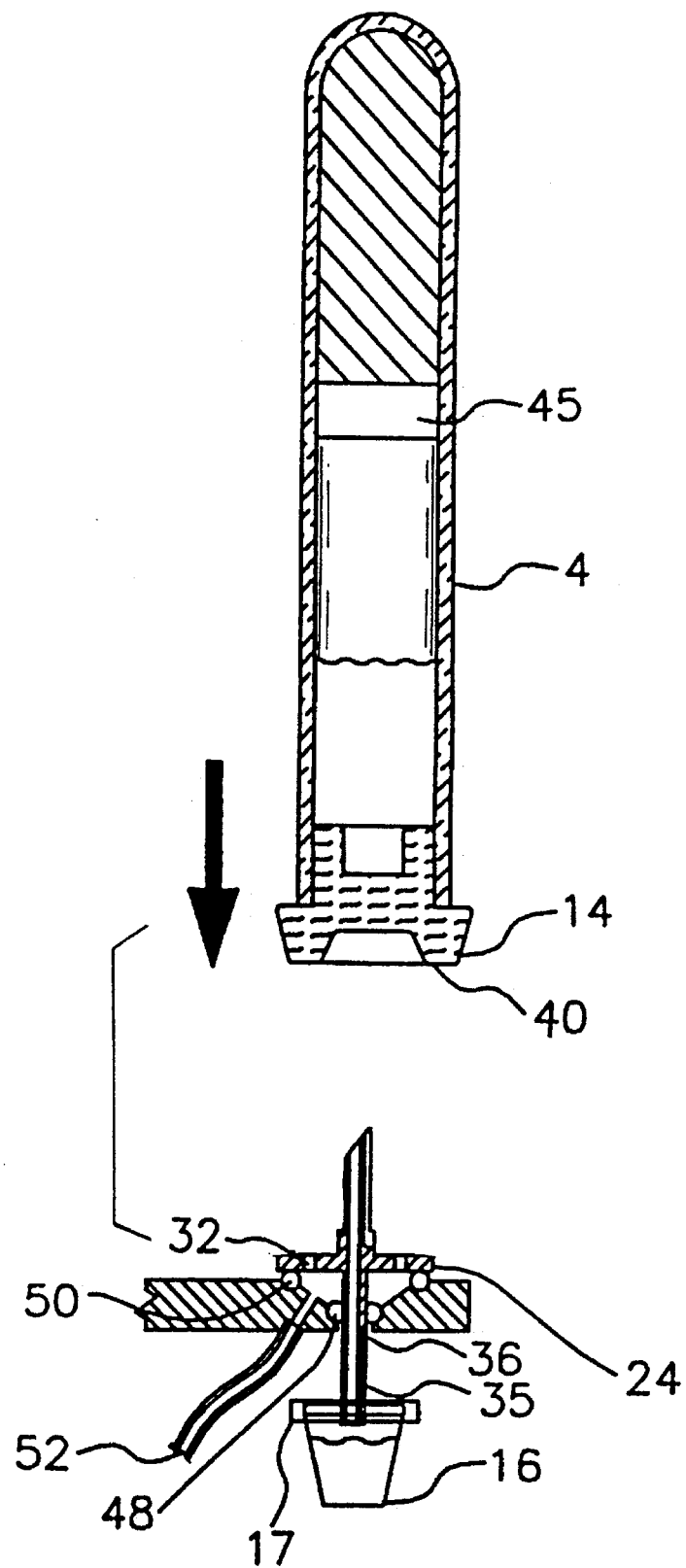
FIG. 17 shows a centrifuged blood collection tube being inserted on to a disposable pipetter that is already in the cap of an analyzer cup.

Variations of the invention which may be advantageous in some applications would result from slightly changing the order in which the aliquotting steps are completed. For example, although the preferred embodiment described above shows disposable pipetter 24 being inserted into blood tube 4 prior to blood collection tube 4 being inverted, these steps could be reversed so that blood tube 4 is first inverted over analyzer cup 16 and then disposable pipetter 24 is inserted. A related variation to the invention would first see disposable pipetter 24 inserted through cap 17 of analyzer cup 16 followed by the insertion of blood tube 4 on to disposable pipetter 24, as shown in FIG. 17. In this variation, a new disposable pipetter 24 would be used for each analyzer cup 16. A further variation would see disposable pipetter 24 incorporated into cap 17 of analyzer cup 16.

Accordingly, the invention is to be limited only by reference to the appended claims.

We claim:

1. Apparatus for dispensing a liquid from a closed liquid sample collection tube into a closed sample cup comprising:

(a) an elongated closure piercing member having a first end shaped for piercing a stopper of a liquid sample collection tube and extending into the tube and a second end shaped for piercing a stopper of a sample cup and extending into the sample cup;

(b) liquid path means located within the closure piercing member for defining an opening through both stoppers when the closure piercing member is inserted through the stopper of the liquid sample collection tube and the stopper of the sample cup;

(c) first gas passage means to allow gas to be introduced into the interior of the liquid sample collection tube for the purpose of dispensing liquid from the tube;

(d) input means to produce a control signal indicative of a specified quantity of liquid to be dispensed; and (e) controlling means responsive to the control signal to meter the introduction of gas into the liquid sample collection tube without moving the closure piercing member relative to the tube, so that the specified quantity of liquid is dispensed into the closed sample cup.

2. The apparatus of claim 1, further including second gas passage means to allow gas to escape from the sample cup when liquid is dispensed into the sample cup from the collection tube.

3. The apparatus of claim 2 wherein the closure piercing member includes a conduit having an exterior surface, and wherein the liquid path means includes an inner bore extending between opposing ends of the conduit and wherein the first and second gas passage means include a groove formed in the exterior surface of the conduit.

4. The apparatus of claim 3 further including a disk-shaped member attached to the conduit between the ends of the conduit and having at least one opening formed therethrough.

5. Apparatus for dispensing a liquid from a closed liquid sample collection tube into a closed sample cup comprising:

(a) a closure piercing member having a first end shaped for piercing a stopper of a liquid sample collection tube and extending into the tube and a second end shaped for piercing a stopper of a sample cup and extending into the sample cup;

(b) a substantially straight liquid path located within the closure piercing member for defining an opening through both stoppers when the closure piercing member is inserted through the stopper of the liquid sample collection tube and the stopper of the sample cup;

(c) a first gas passage connected to a gas supply actuator that is responsive to a third control signal for directing a metered amount of gas to be introduced into the interior of the liquid sample collection tube for the purpose of dispensing liquid from the tube;

(d) sensing means to determine the amount of liquid contained within the liquid sample collection tube and to produce a first signal indicative of that amount;

(e) input means to produce a second signal indicative of a specified quantity of liquid to be dispensed; and (f) controlling means responsive to the first and second control signals to provide the third control signal to the gas supply actuator thereby to regulate the introduction of gas into the liquid sample collection tube so that the specified quantity of liquid is dispensed.

6. The apparatus of claim 5, further including second gas passage means to allow gas to escape from the sample cup when liquid is dispensed into the sample cup from the collection tube.

7. Method of dispensing a liquid from a liquid sample collection tube closed at one end by a stopper into a sample cup closed with a stopper, comprising the steps of:

(a) inserting a dual conduit member through the stopper of a liquid sample collection tube containing a liquid and through the stopper of a sample cup and thereby establishing a liquid passageway between the collection tube and the sample cup and a gas passageway into the collection tube;

(b) positioning the collection tube in an inverted orientation so that the liquid contained in the collection tube is above the stopper;

(c) connecting the gas passageway to a metered gas supply for introducing gas into the collection tube through the gas passageway; and (d) introducing a metered volume of gas into the collection tube through the gas passageway thereby dispensing a volume of liquid out of the collection tube and into the sample cup through the liquid passageway.

8. The method of claim 7 including after dispensing the volume of liquid, disconnecting the gas passageway from the gas supply, removing the dual conduit member from the stopper of the sample cup and leaving the dual conduit member with the collection tube.

9. The method of claim 7 wherein the dual conduit member is inserted through the stopper of the sample cup before being inserted through the stopper of the collection tube.

* * * * *